(12) United States Patent
Nakano et al.

(10) Patent No.: US 9,586,882 B2
(45) Date of Patent: Mar. 7, 2017

(54) METHOD FOR PRODUCING CYCLOALKYL ALKYL ETHER COMPOUND

(71) Applicant: ZEON CORPORATION, Tokyo (JP)

(72) Inventors: Yasushi Nakano, Tokyo (JP); Takashi Sasanuma, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 14/780,316

(22) PCT Filed: Mar. 26, 2014

(86) PCT No.: PCT/JP2014/058679
§ 371 (c)(1),
(2) Date: Sep. 25, 2015

(87) PCT Pub. No.: WO2014/157412
PCT Pub. Date: Oct. 2, 2014

(65) Prior Publication Data
US 2016/0052848 A1    Feb. 25, 2016

(30) Foreign Application Priority Data

Mar. 29, 2013  (JP) .................................. 2013-075151

(51) Int. Cl.
*C07C 41/06*    (2006.01)

(52) U.S. Cl.
CPC .......... *C07C 41/06* (2013.01); *C07C 2101/08* (2013.01)

(58) Field of Classification Search
CPC .............................. C07C 2101/08; C07C 41/06
See application file for complete search history.

(56) References Cited

U.S. PATENT DOCUMENTS

2005/0065060 A1* 3/2005 Kin .................... C07B 49/00
510/506

FOREIGN PATENT DOCUMENTS

| EP | 1405840 A1 | 4/2004 |
|---|---|---|
| JP | 59-25345 A | 2/1984 |
| JP | 61-249945 A | 11/1986 |
| JP | 5-163188 A | 6/1993 |
| JP | 11-100342 A | 4/1999 |
| JP | 2004-292358 A | 10/2004 |
| JP | 2004-300076 A | 10/2004 |
| JP | 2005-2067 A | 1/2005 |
| JP | 2005-82510 A | 3/2005 |
| JP | 2006-206536 A | 8/2006 |
| WO | WO 03/002500 A1 | 1/2003 |
| WO | WO 2007/058251 A1 | 5/2007 |

OTHER PUBLICATIONS

International Search Report, issued in PCT/JP2014/058679, dated Apr. 28, 2014.
English translation of the Written Opinion of the International Searching Authority (Form PCT/ISA/237), dated Apr. 28, 2014, for International Application No. PCT/JP2014/058679.
Chinese Office Action dated May 19, 2016, issued in corresponding Chinese Patent Application No. 201480017659.6.
Yongling Yu et al.; Effects of the physical properties of the etherification reaction resin catalyst on using performance; Qilu Petrochemical Technology, vol. 27; No. 3; pp. 185-187, publication dated: Dec. 31, 1999.
Extended European Search Report, issued Oct. 12, 2016, for European Application No. 14775478.2.

* cited by examiner

*Primary Examiner* — Rosalynd Keys
(74) *Attorney, Agent, or Firm* — Birch, Stewart, Kolasch & Birch, LLP

(57) ABSTRACT

The present invention is a method for producing a cycloalkyl alkyl ether compound comprising reacting substituted or unsubstituted cyclopentene or substituted or unsubstituted cyclohexene with an alcohol compound represented by a formula (2): $R^1OH$ (wherein $R^1$ is a substituted or unsubstituted alkyl group having 1 to 10 carbon atoms, or a substituted or unsubstituted cycloalkyl group having 3 to 8 carbon atoms) in a gaseous state in presence of an acidic ion-exchange resin to produce a cycloalkyl alkyl ether compound represented by a formula (1): $R^1—O—R^2$ (wherein $R^1$ is the same as defined above, and $R^2$ is a substituted or unsubstituted cyclopentyl group or a substituted or unsubstituted cyclohexyl group), the acidic ion-exchange resin having a specific surface area of 20 to 50 $m^2/g$, an average pore size of 20 to 70 nm, and a total exchange capacity of 4.8 to 6.0 eq/L-R wet resin.

5 Claims, 2 Drawing Sheets

METHOD FOR PRODUCING CYCLOALKYL ALKYL ETHER COMPOUND

TECHNICAL FIELD

The present invention relates to a method for industrially advantageously producing a cycloalkyl alkyl ether compound that is useful as a solvent for washing electronic parts and precision machinery parts, a chemical reaction solvent, an extraction solvent, a crystallization solvent, an eluent used for chromatography, a solvent used for electronic-electrical materials, a release agent, and the like.

BACKGROUND ART

A method that subjects an olefin and an alcohol to an addition reaction in the presence of a solid acid catalyst to produce an ether has been known. For example, Patent Document 1 discloses a method that utilizes a crystalline aluminosilicate as a catalyst. Patent Document 2 discloses a method that utilizes a special aluminosilicate having a large number of outer-surface acid sites as a catalyst. Patent Document 3 discloses a method that utilizes a heteropolyacid that includes tungsten oxide (for which the average number of crystal water molecules has been adjusted to 3.0 or less per molecule of the heteropolyacid) as a catalyst. Patent Document 4 discloses a method that utilizes an acidic ion-exchange resin having a water content of 5 mass % or less as a catalyst.

However, when producing a cycloalkyl alkyl ether on an industrial scale from an alicyclic olefin (starting material) using the above solid acid catalyst, deterioration in catalytic activity occurs with the passing of time during long-term continuous operation. Therefore, it is necessary to frequently regenerate the catalyst that has deteriorated in activity, or additionally supply or exchange the catalyst.

Patent Document 5 proposes a method that uses an alicyclic olefin having a linear conjugated diene compound content of 10 ppm or less as the raw material, and Patent Document 6 proposes a method that uses an alicyclic olefin having a linear conjugated diene compound content of 10 ppm or less and a cyclic conjugated diene compound content of 10 ppm or less as the raw material in order to solve the above problem.

These methods can suppress deterioration in catalytic activity with the passing of time, but are not necessarily satisfactory in terms of reaction efficiency and productivity.

RELATED-ART DOCUMENT

Patent Document

Patent Document 1: JP-A-59-25345
Patent Document 2: JP-A-61-249945
Patent Document 3: JP-A-5-163188
Patent Document 4: WO2003/2500
Patent Document 5: JP-A-2004-292358
Patent Document 6: WO2007/58251

SUMMARY OF THE INVENTION

Technical Problem

The invention was conceived in view of the above situation. An object of the invention is to provide a method that can produce a cycloalkyl alkyl ether while suppressing deterioration in catalytic activity with the passing of time, and achieving high reaction efficiency even when the raw material feed rate (amount) is increased.

Solution to Problem

The inventors of the invention conducted extensive studies in order to solve the above problem. As a result, the inventors found that it is possible to produce a cycloalkyl alkyl ether with high reaction efficiency in a stable manner (even when the raw material feed rate (amount) is increased) by reacting cyclopentene or a derivative thereof (or cyclohexene or a derivative thereof) and an alcohol compound in a gaseous state in presence of an acidic ion-exchange resin having a specific surface area, an average pore size, and a total exchange capacity that fall within specific ranges. This finding has led to the completion of the invention.

One aspect of the invention provides the following method for producing a cycloalkyl alkyl ether compound (see [1] to [4]).

[1] A method for producing a cycloalkyl alkyl ether compound including reacting substituted or unsubstituted cyclopentene or substituted or unsubstituted cyclohexene with an alcohol compound represented by a formula (2): R'OH (wherein R' is a substituted or unsubstituted alkyl group having 1 to 10 carbon atoms, or a substituted or unsubstituted cycloalkyl group having 3 to 8 carbon atoms) in a gaseous state in presence of an acidic ion-exchange resin to produce a cycloalkyl alkyl ether compound represented by a formula (1): R'—O—R$^2$ (wherein R$^1$ is the same as defined above, and R$^2$ is a substituted or unsubstituted cyclopentyl group or a substituted or unsubstituted cyclohexyl group), the acidic ion-exchange resin having a specific surface area of 20 to 50 m$^2$/g, an average pore size of 20 to 70 nm, and a total exchange capacity of 4.8 to 6.0 eq/L-R wet resin.

[2] The method for producing a cycloalkyl alkyl ether compound according to [1], wherein R$^1$ in the formula (1) is an alkyl group having 1 to 10 carbon atoms, and R$^2$ in the formula (1) is a cyclopentyl group.

[3] The method for producing a cycloalkyl alkyl ether compound according to [1] or [2], wherein the acidic ion-exchange resin has a specific surface area of 35 to 45 m$^2$/g.

[4] The method for producing a cycloalkyl alkyl ether compound according to any one of [1] to [3], wherein the acidic ion-exchange resin has a total exchange capacity of 5.0 to 5.5 eq/L-R wet resin.

Advantageous Effects of the Invention

The method for producing a cycloalkyl alkyl ether compound according to one aspect of the invention can produce a cycloalkyl alkyl ether while suppressing deterioration in catalytic activity with the passing of time, and achieving high reaction efficiency even when the raw material feed rate (amount) is increased.

The method for producing a cycloalkyl alkyl ether compound according to one aspect of the invention can industrially advantageously produce the desired cycloalkyl alkyl ether compound.

DESCRIPTION OF EMBODIMENTS

Figure 1:
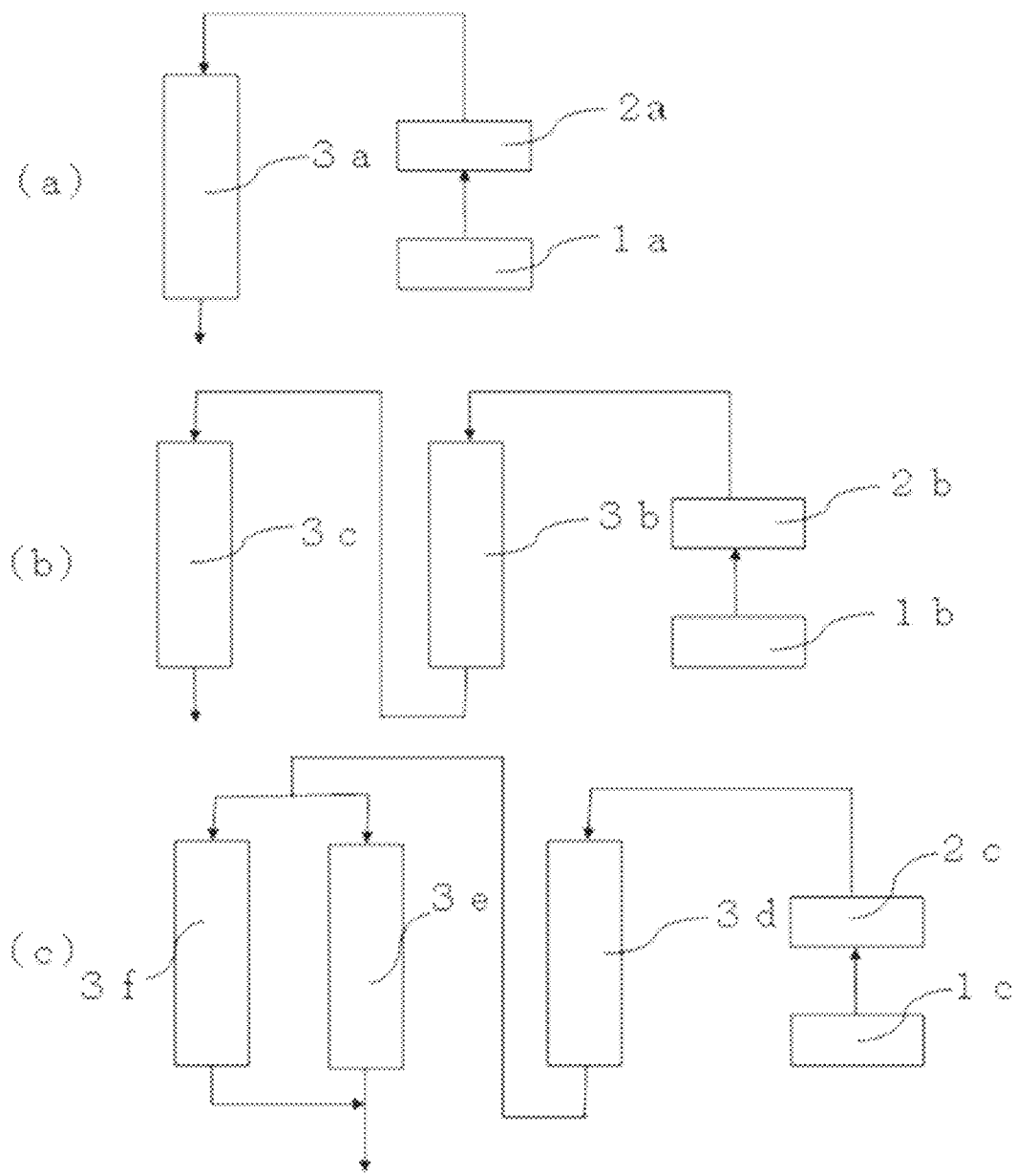
FIG. 1 is a schematic view illustrating a reactor used to implement a production method according to one embodiment of the invention.

The embodiments of the invention are described in detail below.

A method for producing a cycloalkyl alkyl ether compound (hereinafter may be referred to as "production method") according to one embodiment of the invention includes reacting substituted or unsubstituted cyclopentene or substituted or unsubstituted cyclohexene with an alcohol compound represented by the formula (2): $R^1OH$ (hereinafter may be referred to as "alcohol compound (2)") in a gaseous state in presence of an acidic ion-exchange resin to produce a cycloalkyl alkyl ether compound represented by the formula (1): $R^1$—O—$R^2$, the acidic ion-exchange resin having a specific surface area of 20 to 50 $m^2/g$, an average pore size of 20 to 70 nm, and a total exchange capacity of 4.8 to 6.0 eq/L-R wet resin.

The production method according to one embodiment of the invention reacts substituted or unsubstituted cyclopentene or substituted or unsubstituted cyclohexene with the alcohol compound (2).

Examples of a substituent that may substitute cyclopentene or cyclohexene (that is substituted or unsubstituted) used in connection with one embodiment of the invention include an alkyl group having 1 to 4 carbon atoms (e.g., methyl group, ethyl group, n-propyl group, isopropyl group, n-butyl group, t-butyl group, sec-butyl group, and isobutyl group); an alkoxy group having 1 to 4 carbon atoms (e.g., methoxy group, ethoxy group, n-propoxy group, sec-propoxy group, n-butoxy group, t-butoxy group, and sec-butoxy group); an alkylthio group having 1 to 4 carbon atoms (e.g., methylthio group, ethylthio group, n-propylthio group, sec-butylthio group, and t-butylthio group); a halogen atom (e.g., fluorine atom, chlorine atom, bromine atom, and iodine atom); an aryl group (e.g., phenyl group); and the like. Among these, an alkyl group having 1 to 4 carbon atoms is preferable, and a methyl group and an ethyl group are particularly preferable.

Specific examples of substituted or unsubstituted cyclopentene (hereinafter may be referred to as "cyclopentene or a derivative thereof") include cyclopentene; an alkylcyclopentene such as 1-methylcyclopentene, 2-methylcyclopentene, 3-methylcyclopentene, 3-ethylcyclopentene, 3-sec-butylcyclopentene, 2-t-butylcyclopentene, and 1,3-dimethylcyclopentene; an alkoxycyclopentene0 such as 3-methoxycyclopentene, 3-ethoxycyclopentene, 2-sec-butoxycyclopentene, and 3-t-butoxycyclopentene; an alkylthiocyclopentene such as 3-methylthiocyclopentene, 3-ethylthiocyclopentene, 2-sec-butylthiocyclopentene, and 3-t-butylthiocyclopentene; a halogenated cyclopentene such as 1-fluorocyclopentene, 2-chlorocyclopentene, 3-chlorocyclopentene, 2-bromocyclopentene, and 3-bromocyclopentene; an arylcyclopentene such as 1-phenylcyclopentene; and the like.

Specific examples of substituted or unsubstituted cyclohexene (hereinafter may be referred to as "cyclohexene or a derivative thereof") include cyclohexene; an alkylcyclohexene such as 1-methylcyclohexene, 4-methylcyclohexene, 3-ethylcyclohexene, 3-sec-butylcyclohexene, 2-t-butylcyclohexene, and 1,3-dimethylcyclohexene; an alkoxycyclohexene such as 3-methoxycyclohexene, 3-ethoxycyclohexene, 2-sec-butoxycyclohexene, and 3-t-butoxycyclohexene; an alkylthiocyclohexene such as 3-methylthiocyclohexene, 3-ethylthiocyclohexene, 2-sec-butylthiocyclohexene, and 3-t-butylthiocyclohexene; a halogenated cyclohexene such as 1-fluorocyclohexene, 2-chlorocyclohexene, 3-chlorocyclohexene, 4-chlorocyclohexene, 2-bromocyclohexene, and 3-bromocyclohexene; an arylcyclohexene such as 1-phenylcyclohexene and 4-phenylcyclohexene; and the like.

Among these, cyclopentene and cyclohexene are preferable, and cyclopentene is particularly preferable.

The alcohol compound (2) used in connection with one embodiment of the invention is a compound represented by the formula (2): $R^1OH$. $R^1$ in the formula (2) is a substituted or unsubstituted alkyl group having 1 to 10 carbon atoms, or a substituted or unsubstituted cycloalkyl group having 3 to 8 carbon atoms.

Examples of the substituted or unsubstituted alkyl group having 1 to 10 carbon atoms include an alkyl group having 1 to 10 carbon atoms such as a methyl group, an ethyl group, an n-propyl group, an isopropyl group, an n-butyl group, a sec-butyl group, a t-butyl group, an n-pentyl group, a neopentyl group, an n-hexyl group, an n-heptyl group, an n-octyl group, an n-nonyl group, and an n-decyl group; an alkoxyalkyl group such as a methoxymethyl group, a 1-methoxyethyl group, a 2-ethoxy-t-butyl group, and a 2-ethoxy-n-hexyl group; an alkylthioalkyl group such as a methylthiomethyl group, a 1-methylthioethyl group, a 2-methylthio-t-butyl group, and a 4-methylthio-n-hexyl group; a halogenated alkyl group such as a chloromethyl group, a bromomethyl group, a 1-chloroethyl group, a 2-bromo-t-butyl group, and a 2-chloro-n-hexyl group; and the like.

Examples of the substituted or unsubstituted cycloalkyl group having 3 to 8 carbon atoms include a cycloalkyl group having 3 to 8 carbon atoms such as a cyclopropyl group, a cyclobutyl group, a cyclopentyl group, a cyclohexyl group, a cycloheptyl group, and a cyclooctyl group; an alkoxycycloalkyl group such as a 2-methoxycyclopropyl group and a 3-ethoxycyclohexyl group; an alkylthiocycloalkyl group such as a 2-methylthiocyclopropyl group and a 3-ethylthiocyclohexyl group; a halogenated cycloalkyl group such as a 2-chlorocyclopropyl group and a 3-bromocyclohexyl group; and the like.

Specific examples of the alcohol compound (2) include an alcohol compound represented by the formula (2) wherein R' is a substituted or unsubstituted alkyl group having 1 to 10 carbon atoms, such as methanol, ethanol, 2-methoxyethanol, n-propanol, 2-chloro-n-propanol, isopropanol, n-butanol, 3-methylthio-n-butanol, 2-bromo-n-butanol, sec-butanol, isobutanol, t-butanol, n-pentanol, n-hexanol, and cyclopropyl alcohol; and an alcohol compound represented by the formula (2) wherein $R^1$ is a substituted or unsubstituted cycloalkyl group having 3 to 8 carbon atoms, such as cyclopentyl alcohol, 2-chlorocyclopentyl alcohol, cyclohexyl alcohol, cycloheptanol, and cyclooctanol.

It is preferable to use cyclopentene or cyclohexene, and the alcohol compound represented by the formula (2) wherein R' is an alkyl group having 1 to 10 carbon atoms, and it is more preferable to use cyclopentene and the alcohol compound represented by the formula (2) wherein R' is an alkyl group having 1 to 10 carbon atoms, since the advantageous effects of the invention are more effectively obtained.

The alcohol compound (2) is normally used in an amount of 0.002 to 11 mol, and preferably 0.02 to 7 mol, based on 1 mol of cyclopentene or a derivative thereof (cyclohexene or a derivative thereof). The reaction temperature is normally 50 to 150° C., and preferably 80 to 120° C.

In one embodiment of the invention, a specific acidic ion-exchange resin is used as the reaction catalyst.

The term "acidic ion-exchange resin" used herein refers to an insoluble porous synthetic resin that includes a polymer matrix having a fine three-dimensional network structure, and an acidic ion-exchange group. The acidic ion-exchange resin is normally referred to as a cation-exchange resin.

Acidic ion-exchange resins are roughly divided into a gel-type acidic ion-exchange resin, a porous-type acidic ion-exchange resin, and a highly porous-type acidic ion-exchange resin in terms of the geometrical structural plane. Any of these acidic ion-exchange resins may be used.

Examples of the acidic ion-exchange resin include a strongly acidic cation-exchange resin that includes a styrene-based polymer matrix and a sulfonic acid group (ion-exchange group); a weakly acidic cation-exchange resin that includes an acrylic-based polymer matrix or a methacrylic-based polymer matrix, and an acrylic acid group or a methacrylic acid group (ion-exchange group); and the like.

The acidic ion-exchange resin used in connection with one embodiment of the invention has a specific surface area of 20 to 50 $m^2/g$ (preferably 30 to 50 $m^2/g$, and more preferably 35 to 45 $m^2/g$), an average pore size of 20 to 70 nm (preferably 20 to 40 nm, and more preferably 22 to 30 nm), and a total exchange capacity of 4.8 to 6.0 eq/L-R wet resin (preferably 5.0 to 5.5 eq/L-R wet resin, and more preferably 5.2 to 5.4 eq/L-R wet resin).

The above acidic ion-exchange resin (hereinafter may be referred to as "acidic ion-exchange resin A") makes it possible to produce the desired cycloalkyl alkyl ether while suppressing deterioration in catalytic activity with the passing of time, and achieving high reaction efficiency even when the raw material feed rate (amount) is increased.

The term "specific surface area" used herein refers to the surface area ($m^2$) per unit mass (g). A catalyst having a large specific surface area functions well. On the other hand, a catalyst having a large specific surface area may become unstable in the system.

The term "average pore size" used herein refers to the average size (nm) of pores.

The term "total exchange capacity" used herein refers to the total number of ion-exchange groups involved in ion exchange per unit amount of the resin in a wet state (i.e., a normal state of a commercially-available ion-exchange resin). The unit for the total exchange capacity is the number of equivalents per liter (L) of the acidic ion-exchange resin (eq/L-R (R: wet resin)).

The apparent density (g/L-R) of the acidic ion-exchange resin A is normally 500 to 1,000, and preferably 600 to 900. The term "apparent density" normally refers to the density of a solid when the total volume of the solid and inner voids is considered to be the volume of the solid.

The specific surface area, the average pore size, the total exchange capacity, and the apparent density of the acidic ion-exchange resin may be measured and calculated using known methods.

The acidic ion-exchange resin A is normally used in the form of a proton-exchange resin. The acidic ion-exchange resin A can be repeatedly used by subjecting the acidic ion-exchange resin A to a normal regeneration process.

A commercially-available acidic ion-exchange resin having a specific surface area of 20 to 50 $m^2/g$, an average pore size of 20 to 70 nm, and a total exchange capacity of 4.8 to 6.0 eq/L-R wet resin may preferably be used as the acidic ion-exchange resin.

Specific examples of a commercially-available acidic ion-exchange resin that may preferably be used in connection with one embodiment of the invention include CT276 (manufactured by Purolite K.K.); Amberlyst 35 and Amberlyst 36 (manufactured by Organo Corporation); and the like.

It is preferable to use the acidic ion-exchange resin A after dehydration. The water content in the acidic ion-exchange resin A is preferably 5 mass % or less, more preferably 3 mass % or less, and particularly preferably 2 mass % or less. The desired cycloalkyl alkyl ether compound can be produced with high selectivity and a high conversion ratio by utilizing the acidic ion-exchange resin A having a water content of 5 mass % or less.

The water content in the acidic ion-exchange resin A may be adjusted to 5 mass % or less by drying the acidic ion-exchange resin A in advance to remove water. The acidic ion-exchange resin A may be dried using an arbitrary method as long as the water content in the acidic ion-exchange resin A can be adjusted to 5 mass % or less.

The acidic ion-exchange resin A may be dried using a normal thermal dehydration method (operation). Examples of the thermal dehydration method (operation) include (i) a method that places the acidic ion-exchange resin A in a normal drier, and heats the acidic ion-exchange resin A at 50 to 120° C. (preferably 80 to 100° C.) for several minutes to several hours; (ii) a method that heats and dries the acidic ion-exchange resin A at a given temperature (about room temperature to about 100° C.) for several minutes to several hours in a state in which an inert gas is circulated; (iii) a combination of the method (i) and the method (ii); and the like.

Examples of the inert gas used for the method (ii) include air, nitrogen, argon, helium, hydrogen, an aliphatic hydrocarbon, an aromatic hydrocarbon, and the like. The flow (circulation) rate of the inert gas is not particularly limited, but is normally 1 to 200 $h^{-1}$ in terms of the space velocity based on the gas volume at the heating temperature.

Cyclopentene or a derivative thereof (cyclohexene or a derivative thereof) and the alcohol compound (2) may be brought into contact with each other in the presence of the acidic ion-exchange resin A using an arbitrary method. For example, cyclopentene or a derivative thereof (cyclohexene or a derivative thereof) and the alcohol compound (2) may be brought into contact with each other in the presence of the acidic ion-exchange resin A using a method that adds the acidic ion-exchange resin A to a mixture that includes cyclopentene or a derivative thereof (cyclohexene or a derivative thereof) and the alcohol compound (2) (hereinafter may be referred to as "mixture"), and stirs the mixture (batch method), a method that charges a column with the acidic ion-exchange resin A, and causes the mixture to flow through the column (hereinafter referred to as "reaction column") (flow method), or the like. It is preferable to use the flow method from the viewpoint of work efficiency and capability to continuously purify the reaction product.

The mixture is prepared by mixing cyclopentene or a derivative thereof (cyclohexene or a derivative thereof) and the alcohol compound (2) in a given ratio. In this case, a mixture that includes cyclopentene or a derivative thereof (cyclohexene or a derivative thereof) and the alcohol compound (2) may be prepared in advance, stored in a tank, and fed to the reaction column from the tank in a gaseous state, or cyclopentene or a derivative thereof (cyclohexene or a derivative thereof) and the alcohol compound (2) may be stored in different tanks, separately fed from the different tanks, and mixed immediately before being introduced into the reaction column to prepare the mixture in a gaseous state. It is preferable that the water content in the resulting mixture be as low as possible in order to more efficiently obtain the desired product. The water content in the resulting mixture is preferably 1 mass % or less, and particularly preferably 500 ppm or less.

When using the batch method, given amounts of the acidic ion-exchange resin A, cyclopentene or a derivative thereof (cyclohexene or a derivative thereof), and the alcohol compound (2) are added to a reactor, and the mixture is stirred at a given temperature under a given pressure. In this case, the acidic ion-exchange resin A is normally used in a ratio of 0.01 to 200 parts by weight, preferably 0.1 to 150 parts by weight, and more preferably 1 to 100 parts by weight, based on 100 parts by weight of cyclopentene or a derivative thereof (cyclohexene or a derivative thereof).

When using the batch method, cyclopentene or a derivative thereof (cyclohexene or a derivative thereof) and the alcohol compound (2) may be used in an arbitrary ratio. Note that it is preferable to use the alcohol compound (2) in excess with respect to cyclopentene or a derivative thereof (cyclohexene or a derivative thereof). Specifically, since the mixture is heated for a long time when using the batch method, a polymer of cyclopentene or a derivative thereof (cyclohexene or a derivative thereof) may be produced if the mixture is reacted in a state in which cyclopentene or a derivative thereof (cyclohexene or a derivative thereof) is used in excess with respect to the alcohol compound (2). Cyclopentene or a derivative thereof (cyclohexene or a derivative thereof) and the alcohol compound (2) are normally used in a molar ratio (cyclopentene or derivative thereof (cyclohexene or derivative thereof)/alcohol compound (2)) of 1/1 to 1/50, preferably 1/1 to 1/30, and more preferably 1/1 to 1/20.

When using the flow method, the mixture is caused to flow through the reaction column. In this case, a column provided with a heater is used as the reaction column, and the mixture is caused to flow through the reaction column heated to a given temperature (reaction temperature) in a gaseous state.

As illustrated in FIG. 1 (see (a)), the mixture may be fed from a mixture storage tank $1a$ to a heater-vaporizer $2a$, vaporized using the heater-vaporizer $2a$, and fed to a reaction column $3a$ in a gaseous state to effect a gas phase-solid phase reaction, for example. When a plurality of reaction columns are used, it is preferable to maintain the reaction columns and a pipe that connects the reaction columns at a given temperature.

When using the flow method, a method that effects a reaction using a plurality of reaction columns $3b$ and $3c$ (charged with the acidic ion-exchange resin A) that are connected in series (see (b) in FIG. 1), a method that effects a reaction using a plurality of reaction columns $3d$, $3e$, and $3f$ that are connected in series and parallel (see (c) in FIG. 1), or the like may also be used instead of the method that uses the reaction column $3a$ (charged with the acidic ion-exchange resin A) alone (see (a) in FIG. 1). It is possible to further improve the conversion ratio of cyclopentene or a derivative thereof (cyclohexene or a derivative thereof or the alcohol compound (2)) by utilizing a plurality of reaction columns in combination.

The size of the column is not particularly limited. A column having an arbitrary size may be selected taking account of the reaction scale. Note that a plurality of reaction columns used in combination may be charged with an identical acidic ion-exchange resin A, or may be charged with different acidic ion-exchange resins A.

The mixture may be caused to flow through the reaction column charged with the acidic ion-exchange resin A using a down-flow method that causes the mixture to flow from the upper part of the reaction column ($3b$, $3c$) (see (b) in FIG. 1), or an up-flow method that causes the mixture to flow from the lower part of the reaction column (not illustrated in the drawings). It is preferable to use the down-flow method since the desired product can be obtained with a higher conversion ratio and higher selectivity.

The mixture is normally caused to flow through the reaction column under a pressure from normal pressure to 30 MPa, preferably from normal pressure to 10 MPa, and more preferably from normal pressure to 5 MPa. The space velocity of the mixture when using the flow method is normally 50 to 1,000 $h^{-1}$, and preferably 200 to 800 $h^{-1}$. When a plurality of reaction columns are used, the reaction temperature, the flow rate, and the like may be changed on a reaction column basis.

When using the flow method, cyclopentene or a derivative thereof (cyclohexene or a derivative thereof) and the alcohol compound (2) may be used in an arbitrary ratio. Note that it is preferable to use cyclopentene or a derivative thereof (cyclohexene or a derivative thereof) in excess with respect to the alcohol compound (2). Specifically, since the mixture is heated for only a short time when using the flow method, cyclopentene or a derivative thereof (cyclohexene or a derivative thereof) is not polymerized. However, the amount of dialkyl ether (by-product) produced increases if the alcohol compound (2) is used in excess with respect to cyclopentene or a derivative thereof (cyclohexene or a derivative thereof). Cyclopentene or a derivative thereof (cyclohexene or a derivative thereof) and the alcohol compound (2) are normally used in a molar ratio (cyclopentene or derivative thereof (cyclohexene or derivative thereof)/alcohol compound (2)) of 1/3 to 20/1, preferably 1/3 to 10/1, more preferably 1/3 to 5/1, and still more preferably 1/3 to 3/1.

After completion of the reaction, the desired cycloalkyl alkyl ether compound is isolated from the reaction mixture using a normal separation-purification method (e.g., extraction with a solvent or distillation). The distillation operation may be performed a plurality of times.

Figure 2:
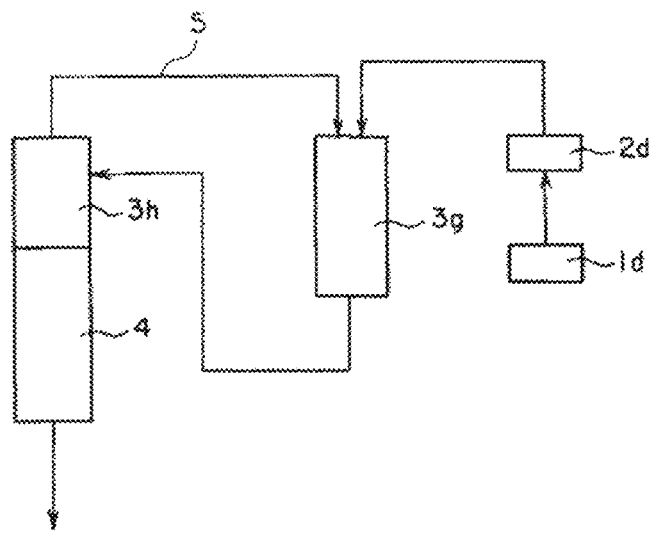
FIG. 2 is a schematic view illustrating a device that includes a reactor and a distillation apparatus used to implement a production method according to one embodiment of the invention.

A known distillation apparatus (e.g., a continuous rectification apparatus provided with a rectifying column) may be used for distillation, for example. As illustrated in FIG. 2, the mixture may be caused to flow through a reaction column $3g$ charged with the acidic ion-exchange resin A, and the resulting reaction mixture may be passed through a reaction column $3h$, and continuously distilled using a distillation apparatus 4 provided with Raschig rings, for example. In this case, unreacted cyclopentene or a derivative thereof (cyclohexene or a derivative thereof) and the alcohol compound (2) can be returned to the reaction column $3g$ through a pipe 5, and reacted again. Therefore, it is possible to obtain the desired product with a higher conversion ratio.

The reaction may be effected in the absence of a solvent, or may be effected in a state in which the mixture is diluted with an inert solvent that dissolves cyclopentene or a derivative thereof (cyclohexene or a derivative thereof) (raw material) and is immiscible with water.

Examples of the solvent include a saturated aliphatic hydrocarbon such as n-butane, n-pentane, n-hexane, n-heptane, n-octane, n-nonane, and n-decane; an aromatic hydrocarbon such as benzene, toluene, ethylbenzene, xylene, anisole, cumene, and nitrobenzene; a saturated alicyclic hydrocarbon such as cyclopentane, an alkyl-substituted cyclopentane, an alkoxy-substituted cyclopentane, a nitro-substituted cyclopentane, cyclohexane, an alkyl-substituted cyclohexane, an alkoxy-substituted cyclohexane, a nitro-substituted cyclohexane, cycloheptane, an alkyl-substituted cycloheptane, an alkoxy-substituted cycloheptane, a nitro-substituted cycloheptane, cyclooctane, an alkyl-substituted cyclooctane, an alkoxy-substituted cyclooctane, and a nitro-substituted cyclooctane; nitrogen; argon; air; helium; and the like. The solvent (diluent) may be used in an arbitrary amount as long as the reaction is not hindered. The solvent is normally used in a ratio of 10 to 90 vol %, and preferably 20 to 80 vol %, based on the total amount of the reaction mixture (reactant).

The above operation makes it possible to produce the desired cycloalkyl alkyl ether represented by the formula (1): $R^1$—O—$R^2$ while suppressing deterioration in catalytic activity with the passing of time, and achieving high reaction efficiency even when the raw material feed rate (amount) is increased.

Note that $R^1$ in the formula (1) is the same as defined above, and $R^2$ in the formula (1) is a substituted or unsubstituted cyclopentyl group (derived from cyclopentene or a derivative thereof) or a substituted or unsubstituted cyclohexyl group (derived from cyclohexene or a derivative thereof).

Specific examples of the substituted or unsubstituted cyclopentyl group and the substituted or unsubstituted cyclohexyl group include a cyclopentyl group and a cyclohexyl group; an alkylcyclopentyl group and an alkylcyclohexyl group such as a 2-methylcyclopentyl group, a 3-ethylcyclohexyl group, a 3-sec-butylcyclopentyl group, and a 2-t-butylcyclohexyl group; an alkoxycyclopentyl group and an alkoxycyclohexyl group such as a 3-methoxycyclopentyl group, a 3-ethoxycyclohexyl group, a 2-sec-butoxycyclopentyl group, and a 3-t-butoxycyclohexyl group; an alkylthiocyclopentyl group and an alkylthiocyclohexyl group such as a 3-methylthiocyclopentyl group, a 3-ethylthiocyclohexyl group, a 2-sec-butylthiocyclopentyl group, and a 3-t-butylthiocyclohexyl group; a halogenated cyclopentyl group and a halogenated cyclohexyl group such as a 2-chlorocyclopentyl group, a 3-chlorocyclopentyl group, a 2-bromocyclohexyl group, and a 3-bromocyclohexyl group; and the like.

EXAMPLES

The invention is further described below by way of examples. Note that the invention is not limited to the following examples.

Production Example 1

Dehydration of Acidic Ion-Exchange Resin

A glass column was charged with 500 mL of a commercially-available acidic ion-exchange resin A ("CT276" manufactured by Purolite K.K., water content: 55 mass %), and the acidic ion-exchange resin was washed by causing 5 L of dehydrated methyl alcohol (water content: 50 ppm) to flow downward through the glass column at a liquid hourly space velocity (LHSV) of 2 $h^{-1}$. 1 L of pure nitrogen was then caused to flow downward through the glass column to remove methyl alcohol remaining between the resin particles. The water content in the dehydrated ion-exchange resin was measured by Karl Fischer coulometric titration, and found to be 1.8 mass %. The resulting acidic ion-exchange resin (hereinafter referred to as "dehydrated acidic ion-exchange resin A") was used for the subsequent reaction.

Note that the water content was measured by Karl Fischer coulometric titration using a moisture meter ("AQ-7" manufactured by Hiranuma Sangyo Co., Ltd.) (generator solution: Hydranal R (manufactured by Sigma-Aldrich) and Aqualyte RS-A (manufactured by Kanto Chemical Co., Inc.), counter solution: Aqualyte CN (manufactured by Kanto Chemical Co., Inc.)).

The following strongly acidic ion-exchange resins were dehydrated in the same manner as described to prepare dehydrated acidic ion-exchange resins B to F. Acidic ion-exchange resin B ("Amberlyst 35" manufactured by Organo Corporation, water content: 55 mass %, water content after dehydration: 1.8 mass %) Acidic ion-exchange resin C ("Amberlyst 36" manufactured by Organo Corporation, water content: 55 mass %, water content after dehydration: 1.8 mass %) Acidic ion-exchange resin D ("Diaion RCP-160M" manufactured by Mitsubishi Chemical Corporation, water content: 47 mass %, water content after dehydration: 1.5 mass %) Acidic ion-exchange resin E ("Diaion PK-228" manufactured by Mitsubishi Chemical Corporation, water content: 40 mass %, water content after dehydration: 1.3 mass %) Acidic ion-exchange resin F ("Lewatit K 2621" manufactured by Lanxess ("SPC118" formerly manufactured by Bayer), water content: 50 mass %, water content after dehydration: 1.6 mass %)

Table 1 shows the specific surface area ($m^2/g$), the average pore size (nm), and the total exchange capacity (eq/L-R) of the acidic ion-exchange resins A to F (i.e., the values listed in the catalog).

Example 1

The following experiment was conducted using the reactor illustrated in FIG. 1 (see (a)).

The reaction column 3a (material: SUS, diameter: 2.54 cm, length: 20 cm) was charged with 72 mL of the dehydrated acidic ion-exchange resin A obtained in Production Example 1, and maintained at 90° C.

A mixture including cyclopentene and methanol (molar ratio: cyclopentene/methanol=1.6/1) was fed from the tank 1 to the heater-vaporizer 2a, heated and vaporized at 90° C. using the heater-vaporizer 2a, and continuously fed to the reaction column 3a at 90° C. under normal pressure (GHSV: 220 to 460 $h^{-1}$). When 1 hour had elapsed after the start of the reaction, the reaction mixture flowing out through the outlet of the reaction column 3a was analyzed by gas chromatography.

Table 1 shows the STY ($kg/hr/m^3$) of cyclopentyl methyl ether produced while changing the GHSV ($h^{-1}$).

Examples 2 and 3 and Comparative Examples 1 to 3

A reaction was effected in the same manner as in Example 1, except that the dehydrated acidic ion-exchange resin was changed as shown in Table 1. Table 1 shows the STY ($kg/hr/m^3$) of cyclopentyl methyl ether produced while changing the GHSV ($h^{-1}$).

Figure 3:
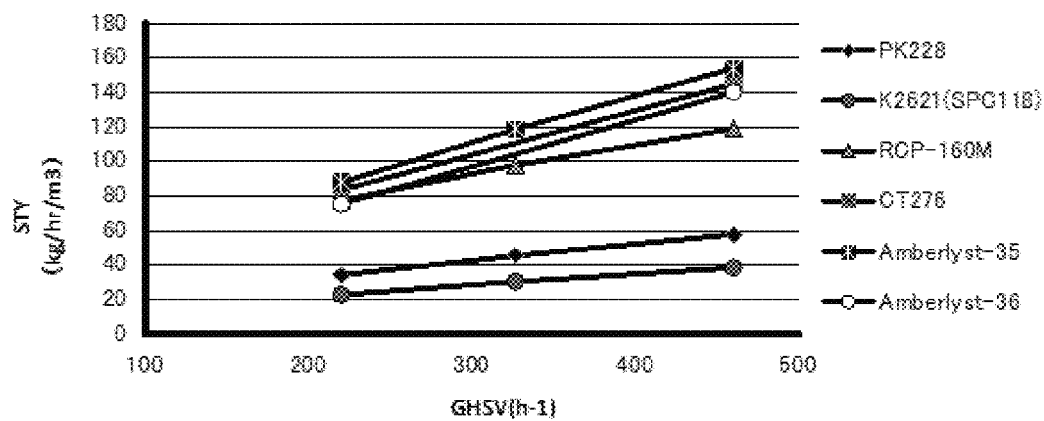
FIG. 3 is a graph showing the relationship between the gas hourly space velocity (GHSV) ($h^{-1}$) (reactant gas flow rate per unit reactor volume) and the amount (kg/hr) of cyclopentyl methyl ether produced per $m^3$ of an acidic ion-exchange resin (space time yield (STY) (kg/hr/$m^3$))

FIG. 3 is a graph showing the relationship between the GHSV ($h^{-1}$) and the STY ($kg/hr/m^3$).

TABLE 1

| | Example 1 | | Example 2 | | | Example 3 | | Comparative Example 1 | | | Comparative Example 2 | | | Comparative Example 3 | | |
|---|---|---|---|---|---|---|---|---|---|---|---|---|---|---|---|---|
| Dehydrated acidic ion-exchange resin | A | | B | | | C | | D | | | E | | | F | | |
| Specific surface area (m²/g) | 30.0 | | 45.0 | | | 33.0 | | 50.0 | | | — | | | 40.0 | | |
| Average pore size (nm) | 60.0 | | 24.0 | | | 24.0 | | 20.0 | | | — | | | 65.0 | | |
| Total exchange capacity (eq/L-R) | 5.2 | | 5.2 | | | 5.4 | | 4.6 | | | 2.1 | | | 1.4 | | |
| GHSV (h⁻¹) | 220 | 460 | 220 | 327 | 460 | 220 | 460 | 220 | 327 | 460 | 220 | 327 | 460 | 220 | 327 | 460 |
| STY (kg/hr/m³) | 83 | 145 | 88 | 119 | 154 | 75 | 140 | 77 | 98 | 119 | 34 | 46 | 58 | 23 | 30 | 38 |

The following were confirmed from the results shown in Table 1.

In Examples 1 to 3, high reactivity was obtained (STY (kg/hr/m³)=75 to 154) even when the GHSV (h⁻¹) was increased.

In Comparative Examples 1 to 3 in which an acidic ion-exchange resin that falls outside the scope of the invention was used, the reactivity decreased as the flow rate increased (Comparative Example 1), or the reactivity was low even when the flow rate was low (Comparative Examples 2 and 3).

REFERENCE SIGNS LIST 1a, 1b, 1c, 1d: Storage tank
2a, 2b, 2c, 2d: Heater-vaporizer
3a, 3b, 3c, 3d, 3e, 3f, 3g, 3h: Reaction column
4: Distillation apparatus
5: Pipe

The invention claimed is:

1. A method for producing a cycloalkyl alkyl ether compound comprising reacting substituted or unsubstituted cyclopentene or substituted or unsubstituted cyclohexene with an alcohol compound represented by a formula (2): $R^1OH$ (wherein $R^1$ is a substituted or unsubstituted alkyl group having 1 to 10 carbon atoms, or a substituted or unsubstituted cycloalkyl group having 3 to 8 carbon atoms) in a gaseous state in presence of an acidic ion-exchange resin to produce a cycloalkyl alkyl ether compound represented by a formula (1): $R^1$—O—$R^2$ (wherein $R^1$ is the same as defined above, and $R^2$ is a substituted or unsubstituted cyclopentyl group or a substituted or unsubstituted cyclohexyl group),
the acidic ion-exchange resin having a specific surface area of 20 to 50 m²/g, an average pore size of 20 to 70 nm, and a total exchange capacity of 4.8 to 6.0 eq/L-R wet resin.

2. The method for producing a cycloalkyl alkyl ether compound according to claim 1, wherein $R^1$ in the formula (1) is an alkyl group having 1 to 10 carbon atoms, and $R^2$ in the formula (1) is a cyclopentyl group.

3. The method for producing a cycloalkyl alkyl ether compound according to claim 1, wherein the acidic ion-exchange resin has a specific surface area of 35 to 45 m²/g.

4. The method for producing a cycloalkyl alkyl ether compound according to claim 1, wherein the acidic ion-exchange resin has a total exchange capacity of 5.0 to 5.5 eq/L-R wet resin.

5. The method for producing a cycloalkyl alkyl ether compound according to claim 1, wherein the acidic ion-exchange resin has a water content of 5 mass % or less.

* * * * *